United States Patent [19]

Schultz et al.

[11] Patent Number: 5,200,626

[45] Date of Patent: Apr. 6, 1993

[54] HIDDEN EXPLOSIVES DETECTOR EMPLOYING PULSED NEUTRON AND X-RAY INTERROGATION

[75] Inventors: Frederick J. Schultz, Oak Ridge, Tenn.; John T. Caldwell, Los Alamos, N. Mex.

[73] Assignee: Martin Marietta Energy Systems, Inc., Oak Ridge, Tenn.

[21] Appl. No.: 500,165

[22] Filed: Mar. 28, 1990

[51] Int. Cl.$^5$ ............................................. G01N 23/222
[52] U.S. Cl. ............................ 250/390.04; 250/358.1
[58] Field of Search ................ 250/358.1, 390.04, 392, 250/359.1, 391; 376/159

[56] References Cited

U.S. PATENT DOCUMENTS

| | | | |
|---|---|---|---|
| 3,832,545 | 8/1974 | Bartko | 250/492.1 |
| 3,997,787 | 12/1976 | Fearon et al. | 250/392 |
| 4,251,726 | 2/1981 | Alverez | 250/390.04 |
| 4,851,687 | 7/1989 | Attinger et al. | 376/159 |
| 4,918,315 | 4/1990 | Gomberg et al. | 250/390.04 |
| 4,918,315 | 4/1990 | Gomberg et al. | 250/390.07 |

OTHER PUBLICATIONS

J. T. Caldwell, et al, Los Alamos National Laboratory Report No. LA-10774-MS, "The Los Alamos Second-Generation System for Passive and Active Neutron Assays of Drum-Size Containers," Sep. 1986.
F. J. Schultz, et al, Oak Ridge National Laboratory Report No. ORNL-6103, "Neutron and Gamma-Ray Nondestructive Examination of Contact-Handled Transuranic Waste at the ORNL TRU Waste Drum Assay Facility," Feb. 21, 1985.
C. H. Lavin, New York Times, "New Machines Can Detect Terrorists' Bombs, Usually," Sep. 12, 1989.
J. Yinon, et al, The Analysis of Explosives, pp. 258-263, Pergamon Press, 1981.
"Testimony of Lee Grodzins before the Sub-Committee on Gov. Activities and Transportation" House Gov. Operations Committee, Representative Cardiss Collins, Chair Sep. 26, 1989.

Primary Examiner—Constantine Hannaher
Assistant Examiner—Richard Hanig
Attorney, Agent, or Firm—Joseph A. Marasco

[57] ABSTRACT

Methods and systems for the detection of small amounts of modern, highly-explosive nitrogen-based explosives, such as plastic explosives, hidden in airline baggage. Several techniques are employed either individually or combined in a hybrid system. One technique employed in combination is X-ray imaging. Another technique is interrogation with a pulsed neutron source in a two-phase mode of operation to image both nitrogen and oxygen densities. Another technique employed in combination is neutron interrogation to form a hydrogen density image or three-dimensional map. In addition, deliberately-placed neutron-absorbing materials can be detected.

29 Claims, 6 Drawing Sheets

HIDDEN EXPLOSIVES DETECTOR EMPLOYING PULSED NEUTRON AND X-RAY INTERROGATION

The U.S. Government has rights in this invention pursuant to Contract No. de-ac05-84or21400 between the United States Department of Energy and Marietta Energy Systems, Inc.

BACKGROUND OF THE INVENTION

The present invention relates to the detection of explosives hidden in packages, particularly small amounts of modern, highly-explosive, nitrogen-based plastic explosives hidden in airline bags.

The detection of explosive devices hidden in airline baggage is a significant problem, particularly in view of the development of modern plastic explosives which can be formed into various innocent-appearing shapes and which are sufficiently powerful that small quantities can destroy an aircraft in flight. In general, three different screening approaches for the detection of hidden explosives are known and employed to various degrees at certain airports.

The first of these approaches is conventional X-ray imaging. Mere X-ray imaging however is of limited effectiveness, particularly since explosives need not be formed into any particular shape.

The second approach is the use of a so-called vapor sniffer which collects vapors emanating from luggage and analyzes them for the presence of molecules of explosive materials. While such devices are relatively sensitive, they nevertheless cannot detect explosives which are sealed within containers so as to prevent the escape of sufficient vapor quantities for detection.

The third approach involves the detection of nitrogen by means of thermal neutron interrogation. Nitrogen is a component of virtually every practical known high explosive. Thermal neutron interrogation involves exposing baggage to a "sea" of thermal neutrons (or "slow" neutrons having an energy in the order of 0.025 eV). Thermal neutrons combine with the nuclei of nitrogen-14 atoms to produce an energetic form of nitrogen-15 isotope. The energetic nitrogen-15 isotope immediately decays to its ground state, emitting characteristic 10.8 MeV gamma rays in the process. The 10.8 MeV gamma rays are detected as indicator of the presence of nitrogen in the package.

There are, however, a number of problems with such detectors employing thermal neutrons. A typical neutron source is radioactive californium-252 which emits energetic neutrons that are then slowed to thermal energies for reaction with nitrogen-14 nuclei. The use of such a radioactive neutron source introduces logistical problems related to handling and radiation shielding.

Other disadvantages of such systems include a relatively high false-positive rate coupled with the inability to effectively detect small quantities of explosives, such as quantities less than about one or two pounds. In particular, there are a number of materials other than explosives which contain nitrogen, such as wool and leather. If the threshold level of a system employing thermal neutron interrogation is adjusted so as to detect small quantities of nitrogen, then a high false-positive rate results due to the presence of innocent nitrogen-containing materials, leading to the necessity of searching an excessive number of packages by hand, negating the practical effectiveness of the system. If, on the other hand, the threshold level is set high to avoid false-positives, then the likelihood that actual explosives will escape detection is increased, again negating the effectiveness of the system.

SUMMARY OF THE INVENTION

Accordingly, it is an object of the invention to provide methods and systems for detecting explosives hidden in baggage with a high degree of sensitivity, and with a low false-positive rate.

It is another object of the invention to provide such methods and systems which are suitable for use in airports.

It is another object of the invention to provide such systems which can be made portable for use in high-volume areas (airports) when needed, for use in remote locations, and for use at high-risk installations such as U.S. embassies, military bases, post offices, and federal buildings for the purpose of screening incoming packages.

It is yet another object of the invention to provide such methods and systems which minimize hazards from radiation, and which avoid problems inherent in the handling of radioactive materials.

Briefly stated, and in accordance with one overall aspect of the invention, nitrogen density imaging and oxygen density imaging are employed together, based on the recognition that explosives have both high nitrogen and high oxygen densities, while virtually all of the known "false alarm" materials such as nylon, silk, wool, melamine and the like have relatively high nitrogen densities but low oxygen densities.

More particularly, a method for detecting explosive material hidden in a package includes the initial steps, in any order, of employing pulsed thermal neutron interrogation, preferably from a pair of pulsed neutron sources positioned symmetrically on opposites sides of the packages, and 10.8 MeV gamma ray detection to form a nitrogen density image of the package, and employing fast neutron interrogation and 6 and 7 MeV gamma ray detection to form an oxygen density image of the package. Then the images are considered together to determine whether the package likely contains explosive material.

Preferably, the initial steps include first interrogating the package for approximately three seconds at a pulse rate in the order of 100 Hz with a combination of pulsed thermal neutrons and fast neutrons while detecting 10.8 MeV gamma rays to form the nitrogen density image, and next terminating neutron interrogation and detecting 6 and 7 MeV gamma rays for approximately three seconds to form the oxygen density image.

To enhance the method, a further initial step of employing X-rays to form an X-ray image may be included, with the X-ray image then considered together with the nitrogen density and oxygen density images. Similarly, a further initial step of employing neutron interrogation to form a nitrogen density image of the package may be included, with the nitrogen density image then considered together with the other images.

In one embodiment, apparatus for detecting explosive material hidden in a package includes a pulsed neutron source for interrogating the package with thermal neutrons, and preferably a pair of pulsed neutron sources positioned symmetrically on opposite sides of the package. Also included is an array of gamma ray detectors for detecting 10.8 MeV gamma rays emitted by nitrogen atoms within the package as a result of thermal neutron interrogation for forming a nitrogen density image of the package, and for detecting 6 and 7 MeV gamma rays emitted by oxygen atoms within the package following fast neutron interrogation for forming an oxygen density image of the package. Finally, an analysis device is included for determining whether the package likely contains explosive material based on the nitrogen density and oxygen density images.

The apparatus may further include, in combination, an X-ray imaging device for forming an X-ray image of the package, and an array of neutron detectors for producing a hydrogen density image of the package based on scattering of neutrons by hydrogen atoms within the package.

Briefly stated, and in accordance with another overall aspect of the invention, up to four different detection techniques are combined in a single system having the characteristics of high sensitivity and low false-positive rate.

The first technique of the combination is conventional X-ray imaging for forming an X-ray image of a package, either a two-dimensional image, or a three-dimensional image such as may be obtained by a plurality of views.

The second technique of the inventive combination is nitrogen density imaging based on the interrogation of nitrogen-14 atoms with slow (thermal) neutrons to produce gamma rays which are then detected. Significantly, a pulsed neutron source is employed which offers at least three advantages over a steady neutron source such as californium-252. One advantage is that system signal-to-noise ratio is greatly increased because the detector "window" is open for only a brief time, for example 0.7 ms, while the thermal neutron flux is diminishing in intensity but still present following a neutron interrogation pulse. The increased signal-to-noise ratio enables a lower limit of detection for nitrogen to be achieved. A second advantage is that the use of pulsed neutron interrogation enables the use of time coincidence detection techniques to obtain at least a coarse three-dimensional nitrogen density image employing a relatively small number of gamma ray detectors, for example eight to twelve gamma ray detectors, two positioned generally adjacent each defining wall of an interrogation chamber volume. The ability to thus obtain a coarse three-dimensional image with a relatively small number of gamma ray detectors is significant because sodium iodide crystal detectors are relatively expensive. The third advantage is that a pulsed neutron source does not produce neutrons when not in use.

The third technique of the combination is oxygen density imaging based on the detection of 6 and 7 MeV gamma rays following fast neutron interrogation occurring at the same time as the slow neutron interrogation used for nitrogen density imaging.

The fourth technique in the combination of the invention is hydrogen density imaging, preferably at high resolution. Hydrogen is also a component of many explosives, particularly plastic explosives. Hydrogen density imaging involves interrogating the package with fast neutrons, for example from a neutron source providing energies ranging from 2 MeV up to approximately 14 MeV. The nuclei of hydrogen atoms scatter incident neutrons Arrays of position-sensitive detectors on up to all six sides of the detection chamber detect fast neutrons after they have interrogated the package to form a high-resolution hydrogen density image.

In accordance with another aspect of the invention, neutron-absorbing material within the package, deliberately-placed for example, is detected. One detector measures thermal neutron interrogating flux, and another detector which is directional measures neutrons that have reacted with the package. The ratio of these two measurements provides an indicator of neutron-absorbing material. The detection of neutron-absorbing material may be employed in various combinations with the foregoing approaches.

In another embodiment, a method for detecting explosive material hidden in a package includes the initial steps, in any order, of employing X-rays to form an X-ray image of the package, employing pulsed neutron interrogation and gamma ray detection to form a coarse nitrogen density image of the package, and employing fast neutron interrogation to form a hydrogen density image of the package. Then the images are considered together to determine whether the package likely contains explosive material.

The step of employing pulsed neutron interrogation and gamma ray detection to form a nitrogen density image includes employing a plurality of gamma ray detectors and time-coincidence detection referenced to the timing of the neutron pulses. Sodium iodide crystals are preferably employed as gamma ray detectors. The step of employing of neutron interrogation to form a hydrogen density image of the package preferably includes employing an array of position-sensitive helium-3 neutron detector tubes.

In yet another embodiment, apparatus includes an X-ray imaging device for forming an X-ray image of the package, a pulsed neutron source for interrogating the package, an array of gamma ray detectors synchronized with the pulsed neutron source for detecting gamma rays emitted by nitrogen atoms within the package as a result of neutron interrogation for forming a nitrogen density image of the package, an array of neutron detectors for producing a hydrogen density image of the package based on scattering of neutrons by hydrogen atoms within the package, and an analysis means for determining whether the package likely contains explosive material based on X-ray, nitrogen density and hydrogen density images.

Preferably, the pulsed neutron source comprises a zetatron, and the gamma ray detectors comprise sodium iodide crystals. Preferably, the neutron detectors comprise helium-3 tubes.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION OF THE PREFERRED EMBODIMENTS

Figure 1:
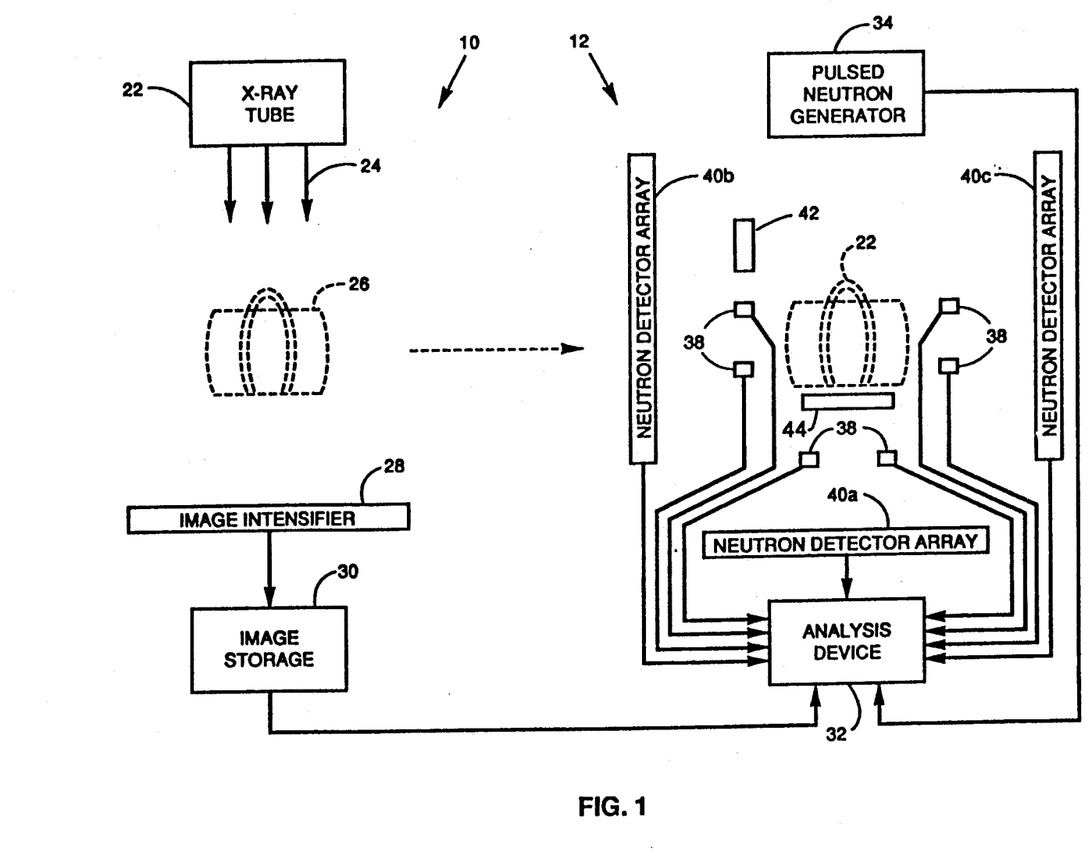
FIG. 1 is a highly schematic conceptual depiction of the invention.

Referring now to the drawings wherein like reference numerals refer to corresponding elements throughout the various views, FIG. 1 depicts a two-stage system including an X-ray interrogation stage generally designated 10 and a neutron interrogation stage generally designated 12. It will be appreciated, however, that the two stages 10 and 12 may be combined in a single station. It will be further appreciated that, in the event two separate stages are employed, the order thereof may be reversed.

The X-ray interrogation stage 10 serves to perform conventional X-ray imaging, and accordingly is not described in detail herein. It may be noted, however, that the combination of X-ray images with images resulting from neutron interrogation, described in detail hereinbelow, is one aspect of the invention to provide comprehensive hidden-explosive detection methods and systems having the characteristics of high sensitivity and a low false-positive rate.

The neutron interrogation stage 12 can have various forms, and can include the capabilities of nitrogen density imaging, oxygen density imaging and hydrogen density imaging in various combinations. In addition, neutron absorbing materials can be detected, providing protection against terrorists who might attempt to defeat measurement systems by wrapping an explosive in a neutron absorber. The neutron interrogation stage 12 employs both thermal and fast neutrons. One or two zetatron neutron generators are employed to directly produce fast 14 MeV neutrons, and moderating materials including lead, graphite and polyethylene slow the fast neutrons to thermal energies of in the order of 0.025 eV.

It is well known that nitrogen is a component of virtually every practical known high explosive, and this fact is exploited by known systems which employ thermal neutrons to detect nitrogen-14 atoms. Unfortunately there are a number of non-explosive materials which contain nitrogen, and the presence of these materials can cause "false alarms" in a hidden-explosive detecting system which relies primarily on detecting and imaging nitrogen.

Figure 2:
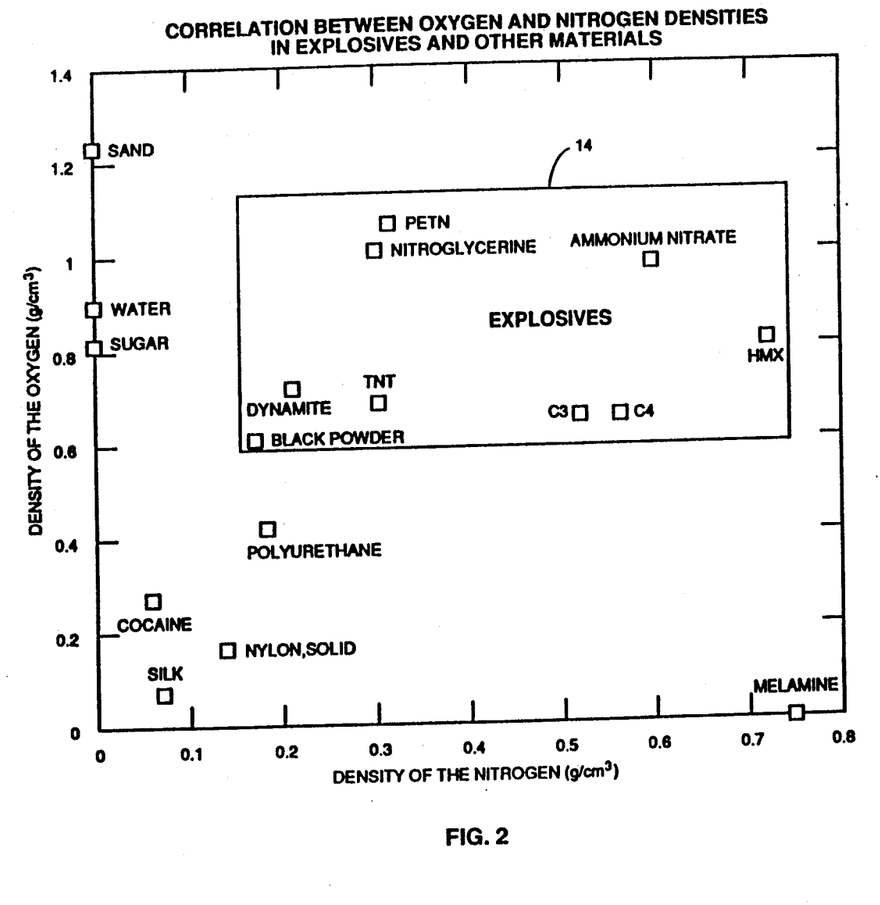
FIG. 2 is a plot depicting the correlation between oxygen and nitrogen densities in various explosives and other materials.

FIG. 2 illustrates the importance of detecting and imaging both nitrogen and oxygen. In particular, FIG. 2 is a correlational plot of oxygen density versus nitrogen density of various materials. The explosives are seen to lie within an "island" 14 of uniquely high nitrogen and oxygen densities. In accordance with the invention, this "island" 14 is detected to reliably detect explosives, while providing almost total discrimination against known "false alarm" materials such as nylon, silk, wool, melamine, and the like that are difficult to discriminate from explosives if only the nitrogen content is analyzed.

Before describing the specific apparatus in detail, several techniques of the invention are described next.

Nitrogen detection and nitrogen density imaging involve interrogating packages with thermal neutrons having an energy of in the order of 0.025 eV. Thermal neutrons combine with the nuclei of nitrogen-14 atoms to produce an energetic form of nitrogen-15 isotope. The energetic nitrogen-15 isotope immediately decays to its ground state, emitting a 10.8 MeV gamma ray. Thus 10.8 MeV gamma rays are detected as an indicator of the presence of nitrogen in the package, and for forming a nitrogen density image.

This process is represented by the following equations:

The oxygen density of materials such as hidden explosives can be imaged employing fast 14 MeV neutrons and detection of 6 and 7 MeV gamma rays. In particular, fast neutrons combine with oxygen-16 atoms to produce transient highly excited atoms of oxygen-17 isotope The oxygen-17 immediately decays, while emitting a proton, to a nitrogen-16 isotope, which is radioactive with a half-life of 7.1 seconds. The nitrogen-16 thus decays, over a period of seconds, to the first and higher excited states of oxygen-16, by a decay process involving beta ray emission and a neutron converting to a proton. The oxygen-16 excited states in turn decay with instantaneous 6 and 7 MeV gamma rays.

This process is represented by the following equations:

and

In accordance with the invention, a two-phase operation cycle is employed to efficiently image both nitrogen and oxygen densities. Each of the two phases has a duration of approximately three seconds. Pulsed neutron interrogation occurs during the first phase only, and gamma ray detection occurs during both phases.

More particularly, during the first phase, one or a pair of zetatron 14 MeV neutron generators are operated in a 100 Hz pulsing mode. During this phase, some of the pulsed 14 MeV neutrons combine with oxygen-16 atoms in the package to produce the nitrogen-16 isotope with a 7.1 second half-life as described above, while the bulk of the 14 MeV neutrons reach thermal energies to react with nitrogen-14 atoms, resulting in the emission of characteristic 10.8 MeV gamma rays. During the first phase, there is an approximately 10 ms interval between neutron pulses, and during these intervals thermal neutron flux results in the emission and detection of the 10.8 MeV gamma rays indicating the presence of nitrogen.

During the second phase, the neutron generator is turned off. Residual decay of the radioactive nitrogen-16 isotope (produced by 14 MeV neutrons combining with oxygen-16) to ultimately produce 6 and 7 MeV gamma rays occurs as described above, and these gamma rays are detected to form an oxygen density image. The detection of these 6 and 7 MeV gamma rays is eased because there is substantially no competitive radiation during the second phase which the detectors would otherwise have to discriminate against.

The two-phase operation described above yields well-matched counting rates and magnitude for sensitive detection and imaging of both oxygen and nitrogen, greatly facilitating the "island" detection technique described with reference to FIG. 2. In particular, from calculations based on known reaction probabilities, typical size detection system and efficiencies, typical luggage inspection procedures, and with a total interrogation of a billion pulsed 14 MeV neutrons nd subsequent thermalized flux, the net count rates of nitrogen-14 10.8 MeV gamma rays and of oxygen-16 6 and 7 MeV gamma rays are each about 400 counts each for one pound of typical explosive in the FIG. 2 "island" 14.

Referring now, in addition to FIG. 1, to FIGS. 3, 4 and 5, details of exemplary apparatus are described.

Figure 4:
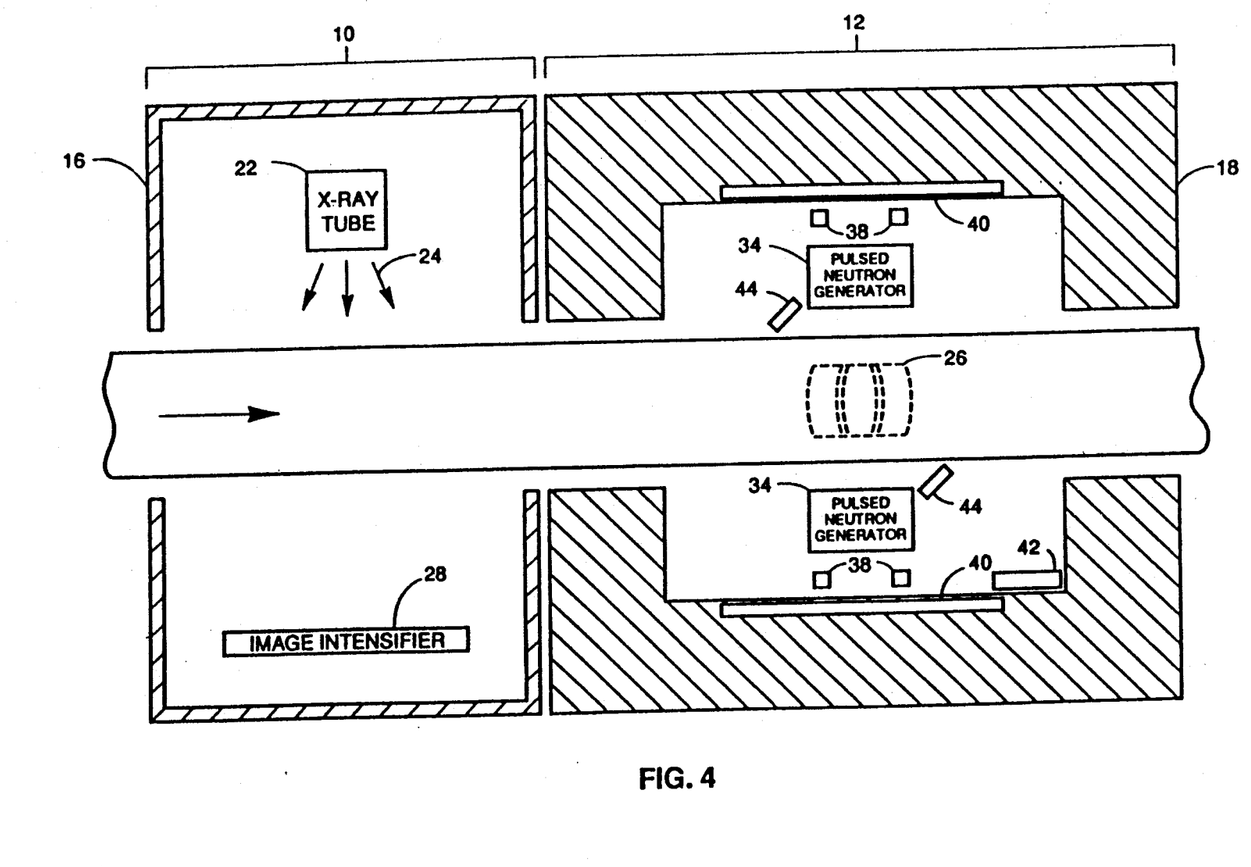
FIG. 4 is a plan view of more specific apparatus in accordance with the invention.
Figure 5:
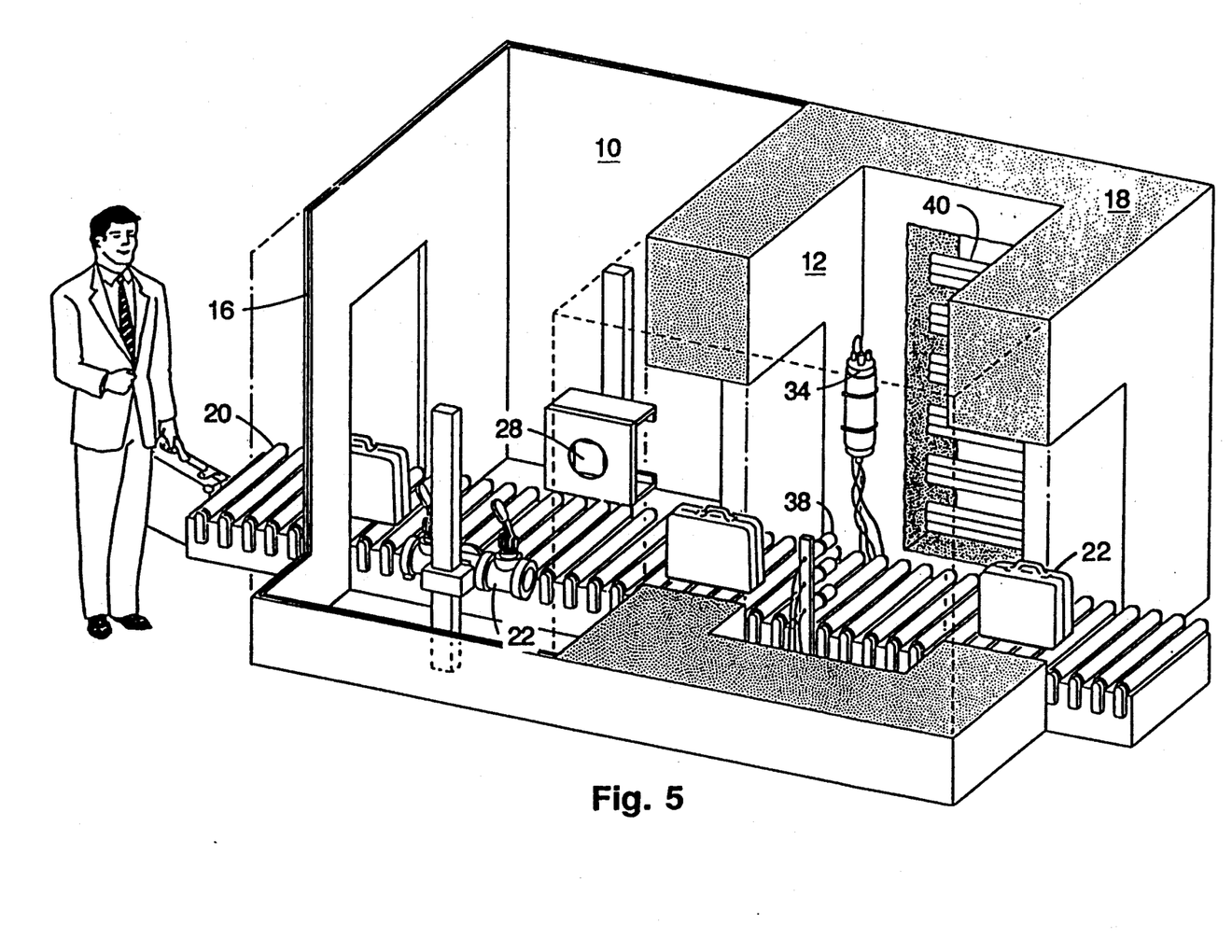
FIG. 5 is a three-dimensional drawing of apparatus in accordance with the invention.

Shown in FIGS. 4 and 5 are appropriate shielding and neutron moderating materials. In particular, shielding around the X-ray interrogation stage 10 comprises one-half inch thick lead wall material 16. Around the neutron interrogation stage 12 are chamber walls 18 which comprise moderating materials including graphite and polyethylene. The walls 18 are from one foot to two feet in thickness. A suitable conveyor 20 transports packages into the apparatus and from the X-ray interrogation stage 10 to the neutron interrogation stage 12.

The X-ray interrogation stage 10 includes an X-ray tube 22 for directing a beam of X-rays represented at 24 through a package represented at 26 for detection by a conventional image intensifier 28 to form a two-dimensional image. The image thus formed is stored in a storage device 30, for example either on videotape or in bit-map form in a computer memory. The image is also accessible by analysis device 32, which may comprise a multi-channel analyzer and an appropriately-programmed computer.

The neutron interrogation stage 12 includes at least one pulsed neutron generator, represented at 34, preferably comprising a zetatron. Briefly, a zetatron neutron generator includes a source of deuterium (hydrogen-2) and tritium (hydrogen-3) ions, in particular a rare earth compound of deuterium and tritium with scandium. A voltage is applied to produce ions, which are accelerated in an exemplary 120,000 volt accelerator, to strike a target of a titanium, deuterium and tritium compound. A fusion reaction then produces neutrons at an energy level of 14 MeV. Such a source can produce approximately one million to three million neutrons per pulse, at a maximum rate of one hundred pulses per second.

Preferably, however, and as represented in FIG. 4, an interrogation geometry is employed that includes a second neutron generator 36. The two zetatron tube assemblies 34 and 36 are located symmetrically on either side of a stream of luggage passing through an inspection station, and are operated simultaneously. This results in improved uniformity of both the fast and thermal neutron interrogations, and greatly improved imaging based on the symmetrical interrogation flux. The cost, including operating and periodic replacement cost, is not much greater with such a "dual source" system than the cost of a single source system. This is because the total zetatron utilization is not increased; each zetatron fires only one-half as much as a single zetatron would to produce the same total flux.

Pulses of fast neutrons are emitted isotropically in all directions and enter the chamber walls 18 (FIGS. 4 and 5) which comprise moderating materials including graphite a polyethylene to slow down the neutrons to produce what may be described as a "sea" of thermal neutrons within the chamber, of which the flux diminishes over a repeatable period of time, for example 0.7 ms.

Accordingly, the pulsed neutron generators 34 and 36, in combination with moderating materials including the chamber walls 18, interrogate the package 26 with both slow thermal neutrons and directly with fast neutrons.

The zetatron pulsed neutron generators 34 and 36 may be constructed so as to beam the fast neutrons towards the package 26 by surrounding the source, except for an outlet in one direction, with a lead and graphite jacket (not shown). The neutrons which do not have direct access through the outlet to the package 26 first encounter a layer of lead and then a layer of graphite. The lead, through an (n,2n) reaction, serves to multiply the neutron flux, while the graphite layer serves to moderate (i.e. slow down) the neutron interrogating flux. Such a jacket increases the thermal neutron flux by perhaps a factor ten, resulting in more efficient operation and a longer lifetime for the zetatron tubes. It also produces a desirable ratio of fast to thermal neutrons, thus deriving the maximum number of fast and slow neutron reactions to facilitate well-matched counting rates and magnitudes for sensitive detection of both nitrogen and oxygen.

As described hereinabove, slow neutrons combine with the nuclei of nitrogen-14 atoms to produce an energetic form of nitrogen-15 isotope, which then decays to its ground state while producing characteristic 10.8 MeV gamma rays. Fast neutrons combine with the nuclei of oxygen-16 atoms to subsequently produce characteristic 6 and 7 MeV gamma rays.

For detecting these gamma rays indicating the presence of nitrogen-14 and oxygen-16 atoms, a plurality of gamma ray detectors 38 are employed, preferably comprising sodium iodide crystal detectors. As may be seen in FIG. 3, the gamma ray detectors 38 are arranged within the inspection chamber volume in spaced detector pairs, one pair on up to each of the six chamber sides. The gamma ray detectors 38 are connected to the analysis device 32, which may include a multi-channel analyzer. By employing time-coincidence detection techniques, synchronized with the pulsing of the sources 34 and 36, at least a coarse three-dimensional nitrogen density image or density map, or at least a total nitrogen inventory, can be obtained with a relatively few number of gamma ray detectors 38, for example from eight to twelve such detectors. Employing the two-phase operation cycle described hereinabove, both nitrogen and oxygen densities are imaged during a time interval of approximately six seconds.

Figure 3:
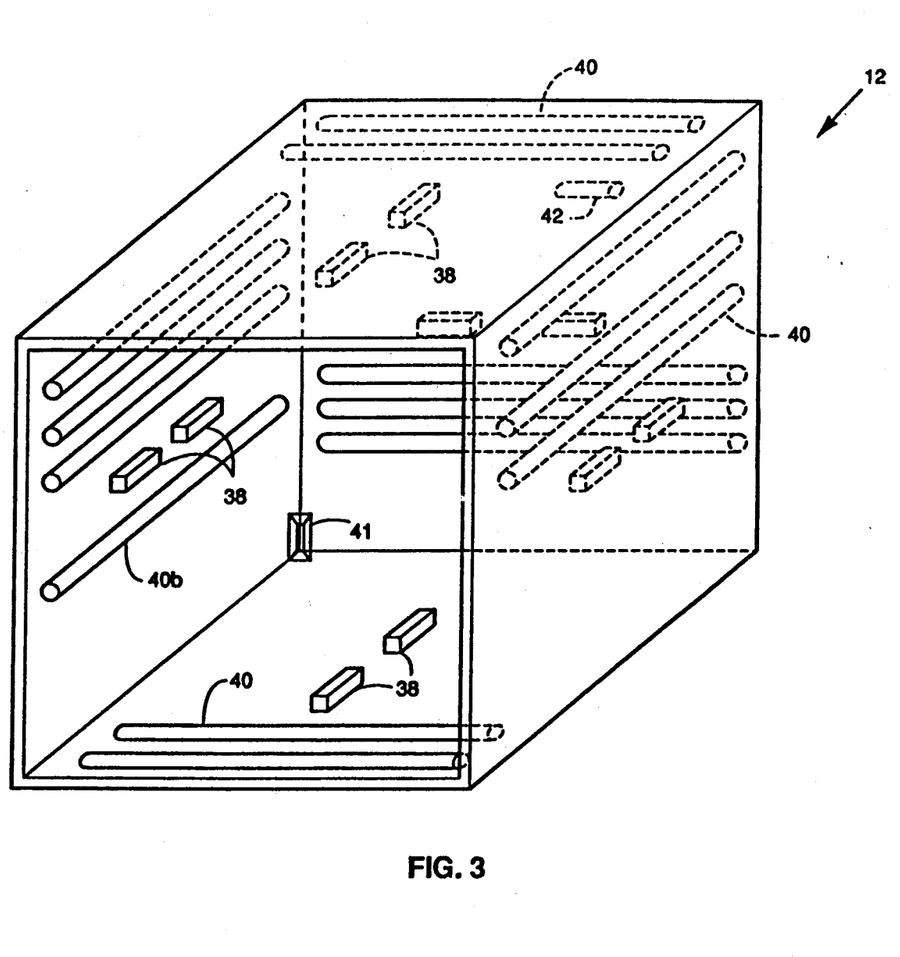
FIG. 3 is a conceptual three-dimensional depiction of a neutron interrogation volume in accordance with the invention.

For producing a hydrogen density image, a plurality of neutron detectors 40 are provided, also connected to the analysis device 32. Preferably, the neutron detectors 40 comprise helium-3 tubes wrapped in appropriate moderating material, or appropriately embedded within the chamber neutron-moderating wall material 18. Helium-3 detector tubes inherently detect slow (thermal) neutrons, but tubes wrapped with a absorber (e.g. cadmium) have incident fast neutrons moderated to slow neutrons for detection by the tube. At the same time any incident slow neutrons are blocked entirely from the helium-3 tube detector As is known, helium-3 tube detectors are capable of detecting position along their length. Thus, a "wall" of such tubes can be employed to form a two-dimensional image at high resolution.

Additionally, to aid in detecting neutron moderator material within the package 26 as described in detail hereinbelow, some of the helium-3 neutron detectors 40 within the walls are bare so as to respond to slow neutrons.

Preferably, such a "wall" of helium-3 detector tubes is positioned on each of the six sides of the inspection chamber (or appropriately embedded in the walls). An array 40a of such neutron detectors positioned opposite the pulsed neutron generator 34 relative to the package 26 position preferentially receives fast neutrons directed through the package 26 and which have not been scattered by hydrogen atoms within the package. Fast neutron detectors 40b and 40c positioned, for example, on the chamber sides receive neutrons scattered from hydrogen atoms, thus providing additional information.

The fast neutron interrogation to form a hydrogen density map or image need not be pulsed. Accordingly, although not presently preferred, a radioactive source such a californium-252 may be employed in addition to the pulsed neutron generator 34.

The analysis device 32 is representative of various techniques which may be employed to analyze and combine the images in order to determine the likelihood the package 22 contains explosives. In essence, signals and images generated as a result of X-ray and pulsed neutron interrogation are combined to produce an analytical "fingerprint" or recognizable pattern of data whereby the presence of explosives may be determined. Preferably, pattern recognition and decision tree software is employed to efficiently automate the screening process, reserving for human intervention only questionable cases.

As a further feature, data can be acquired and analyzed to detect deliberately placed neutron-absorbing material. Thus, there is concern in the field of hidden-explosives detection that a sophisticated terrorist could subvert the measurement of nitrogen by enclosing a concealed explosive within thermal neutron absorbing material, which would result in a low or zero nitrogen density measurement. As a part of the analysis, a luggage neutron "absorption index" can be determined. The "absorption index" can be used both to correct for correspondingly-reduced nitrogen-14 gamma ray intensity for improved images, as well as to detect the outright planned measurement-defeating wrapping of an explosive in neutron absorber.

More particularly, also provided are an unshielded (bare) neutron detector 42 having a helium-3 fill pressure in the order of 0.1 atmosphere for measuring thermal neutron interrogating flux, and a cadmium-collimated helium-3 proportional counter 44 for measuring neutrons which have reacted with the interrogated article or package 26. The cadmium-collimated proportional counter 44 may also be termed a barrel flux monitor 44, and incorporates a cadmium tube of rectangular cross section ahead of a helium-3 detector to provide a highly directional response. Thus the barrel flux monitor 44 discriminates against direct neutron flux from the source 34, while responding to neutrons which have reacted with the package 26. The detector included within the barrel flux monitor 44 has a medium helium-3 fill pressure such that the flux monitor 44 responds to neutron energies in a middle range above thermal energies, but preferably not to fast neutrons. The ratio of the thermal neutron interrogating flux to the neutrons which have reacted with the interrogated package 26 is a direct indication of the quantity of neutron absorbing and moderating material contained in the interrogated package 26.

The foregoing can be expressed as the following equation for the absorption index AI:

$$AI = \frac{\text{interrogating flux monitor response (0.7 to 4.7 ms)}}{\text{barrel flux monitor response (0.7 to 4.7 ms)}}$$

In addition, a moderator index MI may be determined indicating the quantity of neutron-moderating (neutron-slowing) material within the package 26. The responses to moderated neutrons of two neutron detection systems are used to determine the moderator index: (1) cadmium-shielded neutron detectors within the chamber walls, which shielded detectors are insensitive to thermal neutrons; and (2) bare (unshielded) neutron detectors within the chamber walls, which bare detectors are very sensitive to thermal neutron flux. The thermalized neutron flux measured by the bare (unshielded) neutron detectors within the chamber walls depends very strongly on the moderator density within the interrogated package 26.

In addition, to take into account the actual source flux for normalization purposes, the output of the interrogating flux detector 42 may be employed. While the detector 42 actually responds to thermal neutrons and not to fast neutrons, the output of the detector 42 represents the total interrogating flux from the source 34 since thermal neutron flux generated by the source 34 is proportional to the total output of the included zetatron.

To actually calculate the moderator index MI, the normalized ratio of measurements in the form of net count rates from the cadmium-shielded neutron detectors within the chamber walls (shielded totals) to total measurements in the form of net count rates from the cadmium-shielded neutron detectors within the chamber walls in addition to net count rates from the bare detectors within the chamber walls (system totals) is determined. This ratio is normalized so that a value of zero is obtained when no moderator is present. In addition, a small correction is made for self-absorption effects.

Figure 6:
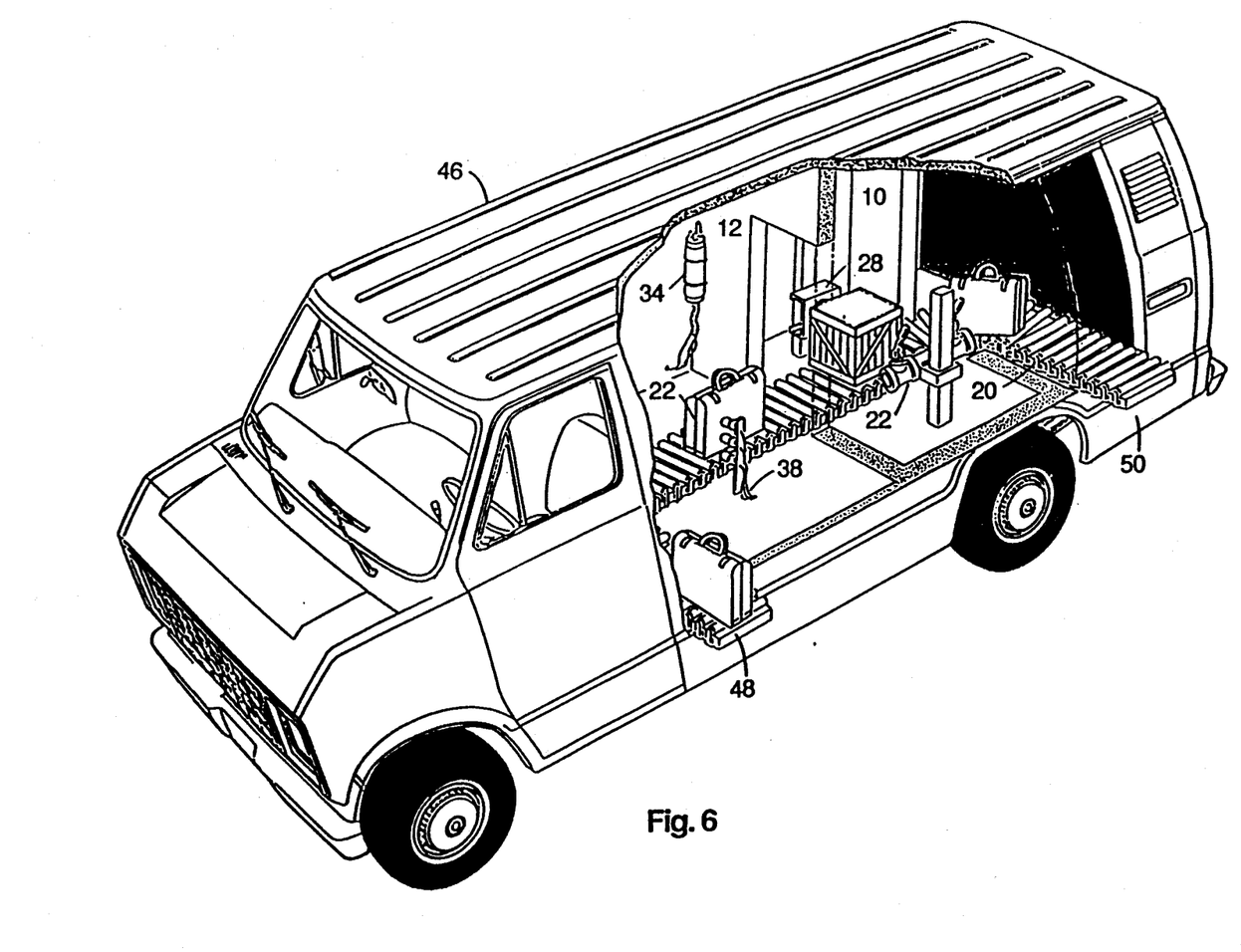
FIG. 6 depicts a variation of the FIG. 5 apparatus carried in a van for convenient portable use in various locations as needed.

An example of a moderator index MI calculation is as follows:

$$MI = \left[1 - \frac{\text{(shielded totals)}}{\text{(system totals)}} \cdot \frac{1}{A_0}\right][A_1 + A_2 \ln(AI)]$$

where: shielded totals is the net count rate of shielded detectors
system totals is the net count rate of shielded plus bare detectors
$A_0$ is a normalization constant calculated based on the measurement of source flux
$A_1$ and $A_2$ are empirical fit constants Finally, FIG. 6 depicts what is essentially the system of FIG. 5 incorporated within a van 46 for portable use on an as-needed basis. For convenience, entry 48 and exit 50 points are provided at right angles to the main path through the system. It will be appreciated that the system of FIG. 6 functions in the same manner as the systems described hereinabove. Thus corresponding reference numerals are employed, and a further description with reference to FIG. 6 is not necessary.

It will be appreciated that a variety of analysis approaches are possible. For example, initially packages may be screened only for nitrogen content, with a relatively low threshold, and then only those packages above the relatively low nitrogen threshold subjected to further scrutiny, such as oxygen density, hydrogen density and X-ray analysis. Various such strategies may be employed to enhance system throughput.

From the foregoing, it will be appreciated that the present invention provides an effective hidden-explosives detector. By performing a number of distinct examinations over a relatively short period of time, and combining the results, a significant and varied quantity of data is acquired, greatly increasing system sensitivity and reducing the false-positive rate. By employing the present invention, explosive quantities as small as 100 grams may be detected, in contrast to a minimum detection limit of one or two pounds with prior systems.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A method for detecting explosive material hidden in a package, comprising:
   the initial steps, in any order, of:
      employing pulsed thermal neutron interrogation and 10.8 MeV gamma ray detection to form a nitrogen density image of the package; and
      employing fast neutron interrogation and 6 and 7 MeV gamma ray detection to form an oxygen density image of the package; and
   then considering the images together to determine whether the package likely contains explosive material.

2. A method in accordance with claim 1, wherein the initial steps comprise:
   first interrogating the package with a combination of pulsed thermal neutrons and fast neutrons for several seconds while detecting 10.8 MeV gamma rays to form the nitrogen density images; and
   next terminating neutron interrogation and detecting 6 and 7 MeV gamma rays for several seconds to form the oxygen density image.

3. A method in accordance with claim 2, wherein the initial step of first interrogating the package with a combination of pulsed thermal neutrons and fast neutrons comprises providing neutron pulses at a rate in the order of 100 Hz.

4. A method in accordance with claim 2, wherein:
   the initial step of first interrogating the package with a combination of pulsed thermal neutrons and fast neutrons while detecting 10.8 MeV gamma rays has a duration of approximately three seconds, and wherein
   the initial step of next terminating neutron interrogation and detecting 6 and 7 MeV gamma rays has a duration of approximately three seconds.

5. A method in accordance with claim 1, which comprises simultaneously employing a pair of pulsed neutron sources positioned symmetrically on opposite sides of the package.

6. A method in accordance with claim 1, which comprises the further initial step of employing X-rays to form an X-ray image of the package.

7. A method in accordance with claim 6, which comprises the further initial step of employing neutron interrogation to form a hydrogen density image of the package.

8. A method in accordance with claim 1, which further comprises measuring and determining the ratio of thermal neutron interrogating flux to detected neutrons which have reacted with the package as an indicator of neutron-absorbing material within the package.

9. Apparatus for detecting explosive material hidden in a package, comprising:
   a pulsed neutron source for interrogating the package with both thermal and fast neutrons;
   an array of gamma ray detectors for detecting 10.8 MeV gamma rays emitted by nitrogen atoms within the package as a result of thermal neutron interrogation for forming a nitrogen density image of the package, and for detecting 6 and 7 MeV gamma rays emitted by oxygen atoms within the package following fast neutron interrogation for forming an oxygen density image of the package; and
   analysis means for determining whether the package likely contains explosive material based on the nitrogen density and oxygen density images.

10. Apparatus in accordance with claim 9, which further comprises an X-ray imaging device for forming an X-ray image of the package.

11. Apparatus in accordance with claim 10, which further comprises an array of neutron detectors for producing a hydrogen density image of the package based on scattering of neutrons by hydrogen atoms within the package.

12. Apparatus in accordance with claim 9, which comprises a pair of pulsed neutron sources positioned symmetrically on opposite sides of the package for interrogating the package with both thermal and fast neutrons.

13. Apparatus in accordance with claim 9, which further comprises:
   an interrogating neutron flux monitor;
   a directional flux monitor for measuring neutrons which have reacted with the packages; and
   means included within said analysis means for detecting neutron-absorbing material within the package based on the ratio of interrogating neutron flux to neutrons which have reacted with the package.

14. A method for detecting explosive material hidden in a package, comprising:
   the initial steps, in any order, of:
      employing X-rays to form an X-ray image of the package,
      employing pulsed neutron interrogation and gamma ray detection to form a nitrogen density image of the package,
      employing neutron interrogation to form a hydrogen density image of the package; and
   then considering the images together to determine whether the package likely contains explosive material.

15. A method in accordance with claim 14, which comprises the further initial step of employing fast neutron interrogation and 6 and 7 MeV gamma ray detection to form an oxygen density image of the package.

16. A method in accordance with claim 14, wherein the step of employing pulsed neutron interrogation and gamma ray detection to form a nitrogen density image includes employing a plurality of gamma ray detectors and time-coincidence detection referenced to the timing of neutron pulses.

17. A method in accordance with claim 16, which includes employing sodium iodide crystals as gamma ray detectors.

18. A method in accordance with claim 14, wherein the step of employing neutron interrogation to form a hydrogen density image of the package includes employing an array of helium-3 neutron detector tubes.

19. A method in accordance with claim 16, wherein the step of employing neutron interrogation to form a hydrogen density image of the package includes employing an array of helium-3 neutron detector tubes.

20. A method in accordance with claim 17, wherein the step of employing neutron interrogation to form a hydrogen density image of the package includes employing an array of helium-3 neutron detector tubes.

21. A method in accordance with claim 14, which further comprises measuring and determining the ratio of thermal neutron interrogating flux to detected neutrons which have reacted with the package as an indicator of neutron-absorbing material within the package.

22. Apparatus for detecting explosive material hidden in a package, comprising:
an X-ray imaging device for forming an X-ray image of the package;
a pulsed neutron source for interrogating the package;
an array of gamma ray detectors synchronized with said pulsed neutron source for detecting gamma rays emitted by nitrogen atoms within the package as a result of neutron interrogation for forming a nitrogen density image of the package;
an array of neutron detectors for producing a hydrogen density image of the package based on scattering of neutrons by hydrogen atoms within the package; and
analysis means for determining whether the package likely contains explosive material based on the X-ray, nitrogen density and hydrogen density images.

23. Apparatus in accordance with claim 22, wherein said pulsed neutron source comprises a zetatron.

24. Apparatus in accordance with claim 22, wherein said gamma ray detectors comprise sodium iodide crystals.

25. Apparatus in accordance with claim 22, wherein said neutron detectors comprise helium-3 tubes.

26. Apparatus in accordance with claim 23, wherein said neutron detectors comprise helium-3 tubes.

27. Apparatus in accordance with claim 24, wherein said neutron detectors comprise helium-3 tubes.

28. Apparatus in accordance with claim 22, which further comprises:
an interrogating neutron flux monitor;
a directional flux monitor for measuring neutrons which have reacted with the packages; and
means included within said analysis means for detecting neutron-absorbing material within the package based on the ratio of interrogating neutron flux to neutrons which have reacted with the package.

29. Apparatus for detecting explosive material hidden in a package, comprising:
an X-ray imaging device for forming an X-ray image of the package;
a pulsed neutron source for interrogating the package with both thermal and fast neutrons;
an array of gamma ray detectors for detecting 10.8 MeV gamma rays emitted by nitrogen atoms within the package as a result of thermal neutron interrogation for forming a nitrogen density image of the package, and for detecting 6 and 7 MeV gamma rays emitted by oxygen atoms within the package following fast neutron interrogation for forming an oxygen density image of the package; and
an array of neutron detectors for producing a hydrogen density image of the package based on scattering of neutrons by hydrogen atoms within the package; and
analysis means for determining whether the package likely contains explosive material based on the X-ray, nitrogen density, oxygen density and hydrogen density images.

* * * * *